(12) United States Patent
Ishida et al.

(10) Patent No.: US 11,957,701 B2
(45) Date of Patent: Apr. 16, 2024

(54) THERAPY AND NEW THERAPEUTIC AGENT FOR BLOOD CANCER

(71) Applicant: Delta-Fly Pharma, Inc., Tokushima (JP)

(72) Inventors: Tatsuhiro Ishida, Tokushima (JP); Kiyoshi Eshima, Tokushima (JP)

(73) Assignee: Delta-Fly Pharma, Inc., Tokushima (JP)

( * ) Notice: Subject to any disclaimer, the term of this patent is extended or adjusted under 35 U.S.C. 154(b) by 127 days.

(21) Appl. No.: 17/424,805

(22) PCT Filed: Jul. 17, 2020

(86) PCT No.: PCT/JP2020/027749
§ 371 (c)(1),
(2) Date: Jul. 21, 2021

(87) PCT Pub. No.: WO2022/014025
PCT Pub. Date: Jan. 20, 2022

(65) Prior Publication Data
US 2022/0313718 A1    Oct. 6, 2022

(51) Int. Cl.
*A01N 43/04* (2006.01)
*A61K 31/635* (2006.01)
*A61K 31/70* (2006.01)
*A61K 31/7068* (2006.01)
*A61P 35/02* (2006.01)

(52) U.S. Cl.
CPC ........ *A61K 31/7068* (2013.01); *A61K 31/635* (2013.01); *A61P 35/02* (2018.01)

(58) Field of Classification Search
None
See application file for complete search history.

(56) References Cited

U.S. PATENT DOCUMENTS

| | | |
|---|---|---|
| 5,616,567 A | 4/1997 | Sasaki et al. |
| 2009/0270340 A1 | 10/2009 | Okabe et al. |
| 2010/0069291 A1 | 3/2010 | Green et al. |
| 2010/0125084 A1 | 5/2010 | Chiao |
| 2011/0207692 A1 | 8/2011 | Green et al. |
| 2018/0303815 A1 | 10/2018 | Merchant et al. |
| 2023/0192752 A1 | 6/2023 | Moon et al. |

FOREIGN PATENT DOCUMENTS

| | | |
|---|---|---|
| CN | 101610776 A | 12/2009 |
| CN | 102088969 A | 6/2011 |
| CN | 108601839 A | 9/2018 |
| CN | 110573620 A | 12/2019 |
| JP | 2559917 B2 | 9/1996 |
| JP | 2010-525042 A | 7/2010 |
| JP | 2011-518761 A | 6/2011 |
| JP | 5570429 B2 | 7/2014 |
| JP | 2018-534298 A | 11/2018 |
| JP | 6895688 B2 | 6/2021 |
| WO | WO-2011/149492 A1 | 12/2011 |
| WO | WO-2019/073296 A1 | 4/2019 |
| WO | WO-2021/079129 | 4/2021 |

OTHER PUBLICATIONS

Yonemura, Yutaka, et al. "Recent advances in the treatment of peritoneal dissemination of gastrointestinal cancers by nucleoside antimetabolites." Cancer science 98.1 (2007): 11-18.*
Iizuka, Kenzo, et al. "Analysis of the prolonged infusion of DFP-10917, a deoxycytidine analog, as a therapeutic strategy for the treatment of human tumor xenografts in vivo." International Journal of Oncology 52.3 (2018): 851-860.*
Guerra, Veronica A., Courtney DiNardo, and Marina Konopleva. "Venetoclax-based therapies for acute myeloid leukemia." Best practice & research Clinical haematology 32.2 (2019): 145-153.*
Akizuki et al., Japanese Society of Internal Medicine Magazine, 2017, 106(3):546-551.
Azuma et al., "2'-C-Cyano-2'-deoxy-1-beta-delta-arabino-pentofuranosylcytosine: A Novel Anticancer Nucleoside Analog that Causes Both DNA Strand Breaks and G2 Arrest," Molecular Pharmacology, Apr. 2001, 59(4):725-731.
Azuma et al., "Nucleosides and Nucleotides. 122. 2'-C-Cyano-2'-deoxy-1-beta-delta-arabinofuranosylcytosine and Its Derivatives. A New Class of Nucleoside with a Broad Antitumor Spectrum," J. Med. Chem., Dec. 1, 1993, 36(26):4183-4189.
Decision to Grant dated May 25, 2021 in JP 2019-077635, with English translation.
Goodman et al., "What are the latest advancements in acute myeloid leukemia therapy?", Future Oncology, Feb. 27, 2017, 13(10):867-871.
Green et al., "Combination of sapacitabine and HDAN inhibitors stimulates cell death in AML and other tumour types," British Journal of Cancer, Oct. 5, 2010, 103:1391-1399.
International Search Report dated Sep. 24, 2020 in PCT/JP2020/027749.
Kadia et al., "An Oral Combination Study of Novel Nucleoside Analogue Sapacitabine and BCL2 Inhibitor Venetoclax to Treat Patients with Relapsed or Refractory AML or MDS," Blood, Nov. 13, 2019, 134(Supp.1):3926, 4 pages.
Niu et al., "Binding of Released Bim to Mcl-1 is a Mechanism of Intrinsic Resistance to ABT-199 which can be Overcome by Combination with Daunorubicin or Cytarabine in AML Cells," Clinical Cancer Research, Apr. 21, 2016, 22(17):4440-4451.

(Continued)

*Primary Examiner* — Patrick T Lewis
(74) *Attorney, Agent, or Firm* — Foley & Lardner LLP

(57) ABSTRACT

An object of the present invention is to provide a new means for treating or ameliorating a blood cancer patient, wherein the new means has high effect and few side effects. The present invention relates to a combined medicine for use in a method for treating or ameliorating a blood cancer patient, comprising 4-amino-1-(2-cyano-2-deoxy-β-D-arabinofuranosyl)-2(1H)-pyrimidinone or a salt thereof and venetoclax or a salt thereof.

8 Claims, 2 Drawing Sheets

(56) References Cited

OTHER PUBLICATIONS

Office Action dated Apr. 20, 2021 in JP 2019-077635, with English translation.
Office Action dated Jan. 19, 2021 in JP 2019-077635, with English translation.
Sami et al., "Current and Future Molecular Targets for Acute Myeloid Leukemia Therapy," Current Treatment Options in Oncology, Jan. 13, 2020, 21(3), 16 pages.
Teh et al., "Enhancing venetoclax activity in acute myeloid leukemia by co-targeting MCL1," Leukemia, 2018 (online Jul. 28, 2017), 32(2):303-312.
Cyclacel Pharmaceuticals Announces First Patient Treated in a Phase 1/2 Study of Sapacitabine and Venetoclax in Relapsed or Refractory AML or MDS Patients, Jul. 22, 2019, 2 pages, www.globenewswire.com/en/newsrelease/2019/07/22/1885652.
Liu et al,. "Sapacitabine, the prodrug of CNDAC, is a nucleoside analog with a unique action mechanism of inducing DNA strand breaks," Chinese Journal of Cancer, 2012, 31(8):373-380.
Office Action dated Dec. 10, 2021 in TW 109124441.
Office Action dated Jun. 29, 2023 in CN 202080019650.4, with English translation.
Extended European Search Report on EP Application No. 20880336.1 dated Feb. 27, 2024, 14 pages.
Huemer et al., "Durable remissions with venetoclax monotherapy in secondary AML refractory to hypomethylating agents and high expression of BCL-2 and/or BIM," Eur J Haematol., 2019, 102:437-441.
Jagan et al., "Bone marrow and peripheral blood AML cells are highly sensitive to CNDAC, the active form of sapacitabine," Advances in Hematology, Jan. 1, 2012, 2012:1-12.
Konopleva et al., "Efficacy and Biological Correlates of Response in a Phase 2 Study of Venetoclax Monotherapy in Patients with Acute Myelogenous Leukemia," Cancer Discov., Oct. 2016, 6(10):1106-1117.

\* cited by examiner

THERAPY AND NEW THERAPEUTIC AGENT FOR BLOOD CANCER

CROSS-REFERENCE TO RELATED APPLICATIONS

This application is the U.S. National Stage of PCT/JP2020/027749 filed Jul. 17, 2020.

TECHNICAL FIELD

The present invention relates to a combined medicine of 4-amino-1-(2-cyano-2-deoxy-β-D-arabinofuranosyl)-2(1H)-pyrimidinone and venetoclax for use in treating or ameliorating a blood cancer patient.

BACKGROUND ART

Blood cancer is a general term for diseases wherein cells in blood are cancerated. Examples thereof include leukemia, malignant lymphoma, and multiple myeloma. Various antitumor agents have been developed today, and blood cancer has not been an incurable illness any longer. Treatment for removing cancer cells completely from bone marrow which is a focus is easily accompanied with intolerable serious side effects even though the patient is a youth with physical strength. Additionally, although bone marrow transplant is required successively, the amount of bone marrow stored in bone marrow banks is not enough, and matching bone marrow is not found easily under the present conditions.

First, 4-amino-1-(2-cyano-2-deoxy-β-D-arabinofuranosyl)-2(1H)-pyrimidinone (hereinafter described as "CNDAC") has a structure in which the 2'β position of the ribose of deoxycytidine is substituted with a cyano group, and is used as an antimetabolite. It is known that CNDAC is phosphorylated by intracellular deoxycytidine kinase, and forms a triphosphorylated form, this is incorporated into DNA strands, the sugar site of the nucleic acid base of CNDAC is then β-cleaved, and the DNA strands are cleaved in G2/M phase of the cell cycle (Patent Literature 1 and Non Patent Literatures 1 and 2). For this reason, it is considered that CNDAC is a clinically effective antitumor agent (Non Patent Literature 3 and Patent Literature 2).

Venetoclax has the effect of selectively binding to and inhibiting Bcl-2. The excessive expression of Bcl-2 is observed in many cancers, and cancer cells prevent the process of spontaneous death or self-destruction (apoptosis) thereby. Venetoclax has the effect of inhibiting this Bcl-2 and regaining the process of apoptosis in cancer cells. Venetoclax has been approved as a therapeutic agent for chronic lymphocytic leukemia (CLL) for which standard treatment is not effective by FDA and been clinically used. The combined therapy of venetoclax with another agent such as azacytidine, decitabine, or cytarabine, which has application to acute myelogenous leukemia (AML), has been approved as a therapeutic agent for untreated elderly AML patients at the end of 2018.

CITATION LIST

Patent Literature

Patent Literature 1: Japanese Patent No. 2559917
Patent Literature 2: Japanese Patent No. 5570429

Non Patent Literature

Non Patent Literature 1: J Med Chem. 1991; 34(9): 2917-9.
Non Patent Literature 2: J Med Chem. 1993; 36(26): 4183-9.
Non Patent Literature 3: Mol Pharmacol. 2001; 59(4): 725-31.

SUMMARY OF INVENTION

Technical Problem

As mentioned above, the treatment of blood cancer is still accompanied with intolerable serious side effects easily, and it is not easy to procure transplantable matching bone marrow.

Then, an object of the present invention is to provide a new means for treating or ameliorating a blood cancer patient, wherein the new means has high effect and few side effects.

Solution to Problem

The present inventors have earnestly examined to solve the above-mentioned problem and consequently found that the administration of CNDAC or a salt thereof and venetoclax or a salt thereof in combination enables treating or ameliorating blood cancer patients by the synergistic effect thereof.

More specifically, the present invention includes the following inventions.

[1] A combined medicine for use in a method for treating or ameliorating a blood cancer patient, comprising CNDAC or a salt thereof and venetoclax or a salt thereof.

[2] The medicine of [1], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.

[3] The medicine of [1] or [2], wherein CNDAC or the salt thereof is parenterally administered.

[4] The medicine of any one of [1] to [3], wherein venetoclax or the salt thereof is orally administered.

[5] The medicine of any one of [1] to [4], wherein the patient is a newly diagnosed and/or elderly patient.

[6] A pharmaceutical composition for use in a method for treating or ameliorating a blood cancer patient, comprising CNDAC or a salt thereof, wherein the pharmaceutical composition is administered in combination with venetoclax or a salt thereof.

[7] A pharmaceutical composition for use in a method for treating or ameliorating a blood cancer patient, comprising venetoclax or a salt thereof, wherein the pharmaceutical composition is administered in combination with CNDAC or a salt thereof.

[8] The pharmaceutical composition of [6] or [7], wherein CNDAC or the salt thereof is parenterally administered.

[9] The pharmaceutical composition of any one of [6] to [8], wherein venetoclax or the salt thereof is orally administered.

[10] The pharmaceutical composition of any one of [6] to [9], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.

[11] The pharmaceutical composition of any one of [6] to [10], wherein the patient is a newly diagnosed and/or elderly patient.
[12] CNDAC or a salt thereof for use with venetoclax or a salt thereof in a method for treating or ameliorating a blood cancer patient.
[13] CNDAC or the salt thereof of [12], wherein CNDAC or the salt thereof is parenterally administered.
[14] CNDAC or the salt thereof of [12] or [13], wherein venetoclax or the salt thereof is orally administered.
[15] CNDAC or the salt thereof of any one of [12] to [14], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.
[16] CNDAC or the salt thereof of any one of [12] to [15], wherein the patient is a newly diagnosed and/or elderly patient.
[17] Venetoclax or a salt thereof for use with CNDAC or a salt thereof in a method for treating or ameliorating a blood cancer patient.
[18] Venetoclax or the salt thereof of [17], wherein venetoclax or the salt thereof is orally administered.
[19] Venetoclax or the salt thereof of [17] or [18], wherein CNDAC or the salt thereof is parenterally administered.
[20] Venetoclax or the salt thereof of any one of [17] to [19], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.
[21] Venetoclax or the salt thereof of any one of [17] to [20], wherein the patient is a newly diagnosed and/or elderly patient.
[22] A method for treating or ameliorating blood cancer, comprising administering CNDAC or a salt thereof and venetoclax or a salt thereof to a patient.
[23] The method of [22], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.
[24] The method of [22] or [23], wherein CNDAC or the salt thereof is parenterally administered.
[25] The method of any one of [22] to [24], wherein venetoclax or the salt thereof is orally administered.
[26] The method of any one of [22] to [25], wherein the patient is a newly diagnosed and/or elderly patient.
[27] Use of CNDAC or a salt thereof and/or venetoclax or a salt thereof in production of a pharmaceutical agent for use in a method for treating or ameliorating blood cancer, comprising administering CNDAC or a salt thereof and venetoclax or a salt thereof to a blood cancer patient.
[28] The use of [27], wherein blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.
[29] The use of [27] or [28], wherein CNDAC or the salt thereof is parenterally administered in the method for treating or ameliorating.
[30] The use of any one of [27] to [29], wherein venetoclax or the salt thereof is orally administered in the method for treating or ameliorating.
[31] The use of [27] to [30], wherein the patient is a newly diagnosed and/or elderly patient.

Advantageous Effects of Invention

According to the present invention, a new means for treating or ameliorating a blood cancer patient can be provided, wherein the new means has high effect and few side effects.

High treatment or ameliorating effect on blood cancer can be obtained by synergistic effect which the combined use of CNDAC or a salt thereof and venetoclax or a salt thereof has.

DESCRIPTION OF EMBODIMENTS

Figure 1:
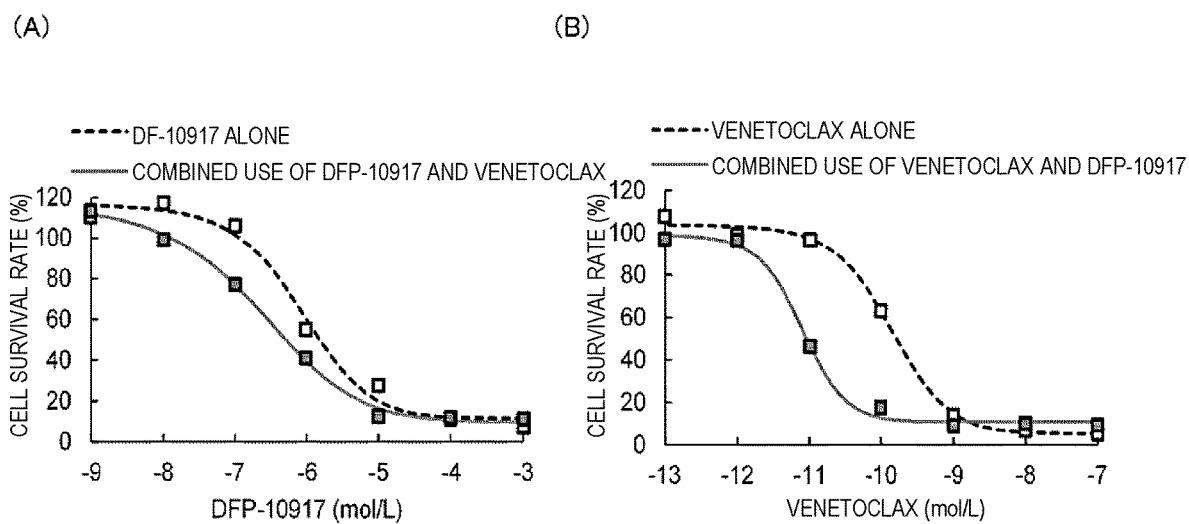
FIG. 1 is a graph showing the results obtained by investigating the cytostatic effects (cell survival rate (%)) of the combined use of DFP-10917 and venetoclax on acute myelogenous leukemia (AML) cells derived from a human. (A) (A) shows the results of the use of DFP-10917 alone and the combined use of DFP-10917 and venetoclax (96.8 pM). (B) (B) shows the results of the use of venetoclax alone and the combined use of venetoclax and DFP-10917 (1.53 µM).

The present invention relates to a method for treating or ameliorating blood cancer, comprising administering a combination of CNDAC or a salt thereof and venetoclax or a salt thereof to a blood cancer patient, and to pharmaceutical agents or a combined medicine used in the method.

In the present invention, "4-amino-1-(2-cyano-2-deoxy-β-D-arabinofuranosyl)-2(1H)-pyrimidinone" or "CNDAC" is a compound represented by the following structural formula:

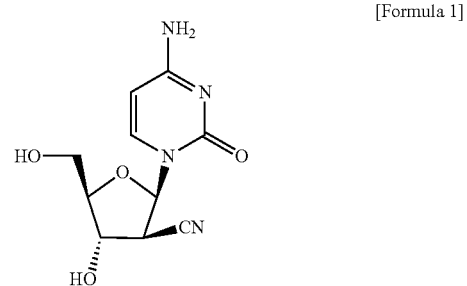 [SMILES: N#C[C@H]1[C@H](O)[C@@H](CO)O[C@H]1n1ccc(N)nc1=O]

[Formula 1]

or a salt thereof. The "salt" is a pharmaceutically acceptable salt, and examples thereof include acid addition salts and basic addition salts. Examples of the "acid addition salts" include hydrochloride, sulfate, nitrate, phosphate, hydrobromid, carbonate, acetate, trifluoroacetate, p-toluenesulfonate, propionate, tartrate, fumarate, malate, maleate, citrate, and methanesulfonate (but are not limited thereto). Examples of the "basic addition salts" include alkali metal salts (sodium salt, potassium salt, and the like), alkaline-earth metal salts (calcium salt, and the like), magnesium salt, and ammonium salt (but are not limited thereto). In the present invention, the hydrochloride or acetate of CNDAC is preferable. More specifically, in the present invention, 4-amino-1-(2-cyano-2-deoxy-β-D-arabinofuranosyl)-2(1H)-pyrimidinone monohydrochloride is particularly preferable. In the present specification, 4-amino-1-(2-cyano-2-deoxy-β-D-arabinofuranosyl)-2(1H)-pyrimidinone monohydrochloride may be described as "DFP-10917".

In the present invention, "venetoclax" is a compound represented by the following structural formula:

[Formula 2]

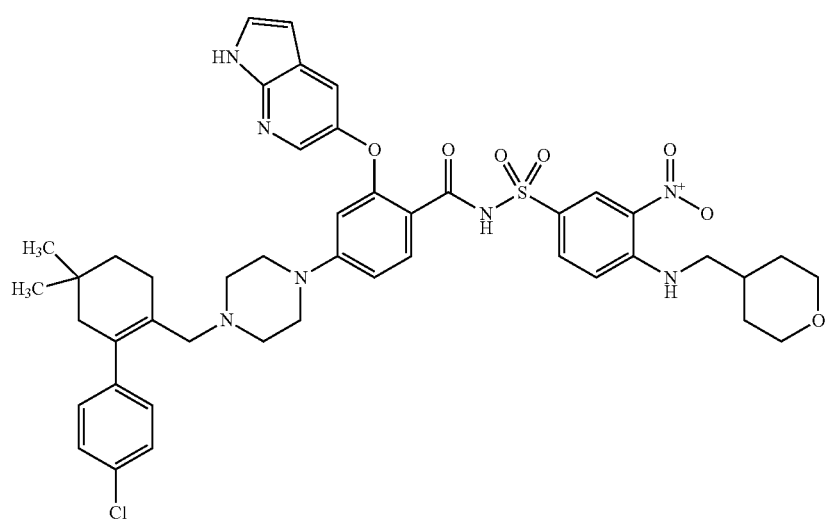

or a salt thereof. The "salt" is a pharmaceutically acceptable salt, and examples thereof include acid addition salts and basic addition salts. Examples of the "acid addition salts" and the "basic addition salts" include the above addition salts.

CNDAC or the salt thereof and venetoclax or the salt thereof may be industrially synthesized in accordance with conventionally well-known techniques, or CNDAC or the salt thereof and venetoclax or the salt thereof marketed for drugs may be used.

In the present invention, "blood cancer" means cancer occurred from the hematopoietic organ. Examples of such blood cancer include but are not limited to acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma. In the present invention, blood cancer is preferably acute myelogenous leukemia (AML).

In the present invention, the "patient" is a blood cancer patient without particular limitation. Although the patient may be a newly diagnosed patient or a recurrent patient, the patient is preferably a newly diagnosed patient; and/or the age of the patient is not particularly limited, and the patient may be an infant patient (5 years old or less), a juvenile patient (6 to 14 years old), a young patient (15 to 34 years old), a patient in the prime of life (35 to 64 years old), or an elderly patient (65 years old or more), but is preferably an elderly patient.

In the present invention, the combined administration of CNDAC or the salt thereof and venetoclax or the salt thereof to a blood cancer patient is performed.

In the present invention, the "combined administration" includes not only the case where components are administered simultaneously but also the case where components are administered sequentially at predetermined intervals over a therapeutic period, respectively, and the case where only any component is administered before and/or after components are administered simultaneously. The administration route and the administration means of the components administered in combination may be the same or different.

Although the dose and administration route of CNDAC or the salt thereof can vary depending on factors such as the type and severity of blood cancer, and the age, weight and condition of the patient, in combined administration with venetoclax or the salt thereof, CNDAC or the salt thereof can be administered in an amount enough to treat or ameliorate blood cancer through any administration route (oral administration or parenteral administration).

For example, the parenteral administration of CNDAC or the salt thereof can be performed in an amount from 1 to 10 mg/m$^2$/day, preferably 4 to 6 mg/m$^2$/day, per 1 m$^2$ of the body surface area of a patient per day in terms of the amount of CNDAC. Examples of the "parenteral administration" include intravenous injection, hypodermic injection, intradermal injection, intramuscular injection, and intravenous drip. The parenteral administration is particularly preferably continuous intravenous infusion. The continuous intravenous infusion means continuous drip administration of the above-mentioned amount over 168 to 336 hours. The administration interval is not particularly limited.

Although the dose and administration route of venetoclax or the salt thereof can vary depending on factors such as the type and severity of blood cancer, and the age, weight and condition of the patient, in combined administration with CNDAC or the salt thereof, venetoclax or the salt thereof can be administered in an amount enough to treat or ameliorate blood cancer through any administration route (oral administration or parenteral administration).

For example, venetoclax or the salt thereof can be orally administered in an amount from 20 to 400 mg/day, preferably 200 to 400 mg/day by dividing it into 1 to 5 doses (for example, 2 or 3) per day every day, every other day, every several days, on 1 day every week, on 2 to 3 days every month, on 1 day every 2 weeks, or on 1 day every month. Alternatively, venetoclax or the salt thereof may be parenterally administered in a dose by which an intravenous level of venetoclax or the salt thereof becomes comparable to that in the case of the oral administration. The "parenteral administration" can be performed by the above-mentioned techniques.

CNDAC or the salt thereof and venetoclax or the salt thereof administered in combination may be provided in the form of separate pharmaceutical agents (or pharmaceutical compositions), or in the form of a combined medicine.

When CNDAC or the salt thereof and venetoclax or the salt thereof are provided as separate pharmaceutical agents (or pharmaceutical compositions), the pharmaceutical agents (or pharmaceutical compositions) are intended to be used in the above-mentioned combined administration, and it can be stated in a column showing "efficacy and effect" or a column showing "use and dose" in its attachment that the pharmaceutical agents (or pharmaceutical compositions) are used in the above-mentioned combined administration. For example, if the pharmaceutical agent (or pharmaceutical composition) is a pharmaceutical agent (or pharmaceutical composition) containing CNDAC or the salt thereof, it can be stated in its attachment that the pharmaceutical agent (or pharmaceutical composition) is "used in combination with venetoclax or a salt thereof" for treating or ameliorating blood cancer. If the pharmaceutical agent (or pharmaceutical composition) is a pharmaceutical agent (or pharmaceutical composition) containing venetoclax or the salt thereof, it can be stated in its attachment that the pharmaceutical agent (or pharmaceutical composition) is "used in combination with 4-amino-1-(2-cyano-2-deoxy-β-D-arabinofuranosyl)-2 (1H)-pyrimidinone or a salt thereof" for treating or ameliorating blood cancer.

The combined medicine may be in the form of a combination drug which contains the components in the same composition, or may be prepared in a form for which the components are provided separately, and produced, packed and distributed as individual packages suitable for combined administration (namely, kit preparations).

In the above-mentioned pharmaceutical agents (or pharmaceutical compositions) and combination medicine, a vehicle, a binder, a disintegrator, a lubricant and the like which are usually used in the production of pharmaceutical agents can be further incorporated besides the above-mentioned components. The above-mentioned pharmaceutical agents (or pharmaceutical compositions) and combination medicine can be produced as dosage forms suitable to designed administration routes.

Examples of the vehicle include sugar (monosaccharides, disaccharides, polysaccharide such as cyclodextrin and alginic acid), metal salts, kaolin, silicic acid, polyethylene glycol, and a mixture thereof.

Examples of the binder include simple syrup, glucose solution, starch solution, gelatin solution, polyvinyl alcohol, polyvinyl ether, polyvinyl pyrrolidone, carboxymethyl cellulose, shellac, methyl cellulose, ethyl cellulose, and a mixture thereof.

Examples of the disintegrator include dry starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, lactose, and a mixture thereof.

Examples of the lubricant include purified talc, stearates, borax, polyethylene glycol, and a mixture thereof.

A diluent, a stabilizer, an isotonizing agent, a pH adjuster, a buffer, a solubilizing agent, a suspending agent, a coloring agent, a flavoring agent, a smell correcting agent, a coating agent, a preservative, an antiseptic, an antioxidant, and the like which are usually used in the production of pharmaceutical agents can be further incorporated optionally if needed.

Examples of the dosage form suitable for oral administration include tablets, pills, capsules, granules, powders, syrups, and suspensions. Pharmaceutical agents having a solid dosage form can be coated if needed (for example, sugar-coated tablets, gelatin-coated tablets, enteric coated tablets, and the like).

Examples of the dosage form suitable for parenteral administration include injections and drips. These dosage forms may be provided in a freeze-dried and storable state, and before use, dissolved in water or in a buffer solution or the like containing a physiological saline solution or the like to prepare a solution at a suitable concentration.

The present invention can be used in combination with an anticancer agent and/or radiotherapy which is used to treat or ameliorate blood cancer. Examples of such an anticancer agent include but are not limited to azacytidine, enocitabine, decitabine, cytarabine, cytarabine ocfosfate, fludarabine, pentostatin, nelarabine, aclarubicin, idarubicin, daunorubicin, doxorubicin, cyclophosphamide, 6-mercaptopurine, methotrexate, busulfan, nimustine, ranimustine, vincristine, vindesine, etoposide, prednisolone, dexamethasone, retinoic acid, tamibarotene, imatinib, nilotinib, dasatinib, mitoxantrone, hydroxyurea, asparaginase, arsenious acid, interferon, and lenalidomide. Here, "Combined administration" is as defined above.

One or more of anticancer agents can be appropriately selected depending on factors such as the type and severity of blood cancer, and the age, weight and condition of the patient.

The present invention can be used for treating or ameliorating blood cancer. More specifically, the present invention relates to a method for treating or ameliorating blood cancer, comprising administering the pharmaceutical agents (or pharmaceutical compositions) or combined medicine of the present invention to a blood cancer patient.

In the present invention, "treating or ameliorating blood cancer" means not only a condition in which blood cancer disappears completely but also a condition in which blood cancer decreases or disappears temporarily or permanently and a condition in which blood cancer is stable without progression (aggravation). For example, "treating or ameliorating cancer" in the present invention includes one or more of a decrease in the number of blood cancer cells, a decrease in the blood cancer marker level, an improvement in symptoms accompanying blood cancer, and the prolongation of criteria such as overall survival time, progression-free survival time and median survival time in the patient as compared with those before the administration or ingestion of the composition of the present invention.

According to the present invention, a blood cancer patient can be treated or ameliorated by administering the above-mentioned pharmaceutical agents (or pharmaceutical compositions) or combined medicine of the present invention. Especially if the patient is a newly diagnosed and/or elderly patient, the effect thereof is observed remarkably, and the survival rate (median survival time and the like) can be enhanced greatly.

The present invention will be specifically described by Examples hereinafter, but the present invention is not limited thereto.

EXAMPLES

Example 1

Effect of Combined Use of 4-amino-1-(2-cyano-2-deoxy-β-D-arabinofuranosyl)-2(1H)-pyrimidinone monohydrochloride (DFP-10917) and Venetoclax In Vitro DFP-10917 alone, venetoclax alone, and the combined use of DFP-10917 and venetoclax were allowed to act on KG-1, SKM-1, OCI-AML-2, MV4-11, and SKNO-1, which are acute myelogenous leukemia (AML) cell lines derived from humans, at various concentrations separately. The number of cells was counted by CellTiter-Glo assay after 72 hours, and the $IC_{50}$ value, which is a concentration at which the number of cells is reduced by 50%, was calculated.

Consequently, the effect of the combined use of DFP-10917 and venetoclax was observed in four types of AML cells (KG-1, OCI-AML-2, MV4-11, and SKNO-1).

Example 2

Effect of Combined Use of DFP-10917 and Venetoclax Under the Condition of a Low Protein Content The effect of the combined use of DFP-10917 and venetoclax was investigated under the condition of a low protein content in view of a high protein binding rate of venetoclax (>99.9%).

DFP-10917 alone, venetoclax alone, and combined use of DFP-10917 and venetoclax were allowed to act on MV4-11, which is an AML cell line, at various concentrations separately. The number of cells was counted by MTT assay using thiazolyl blue tetrazolium bromide after 48 hours, and the $IC_{50}$ value, which is a concentration at which the number of cells is reduced by 50%, was calculated.

FIG. 1 shows the results. In the groups to which DFP-10917 was added (FIG. 1(A)), slight increase in cytostatic effect was seen in the combined use of DFP-10917 and venetoclax (96.8 pM) as compared with DFP-10917 alone. The $IC_{50}$ value was 1.53 μM for DFP-10917 alone, and 0.51 μM for the combined use of DFP-10917 and venetoclax.

Meanwhile, in the groups to which venetoclax was added (FIG. 1(B)), remarkable increase in cytostatic effect was observed in the combined use of venetoclax and DFP-10917 (1.53 μM) as compared with venetoclax alone. The $IC_{50}$ value was 96.8 pM for venetoclax alone, and 9.14 pM for the combined use of venetoclax and DFP-10917. This result shows that the cytostatic effect increased around 10.6 folds by the combined use of venetoclax and DFP-10917 as compared with venetoclax alone. The CI (Combination Index) value was calculated from each $IC_{50}$ value based on the following expression (F. Bruzzese, et al. Clin. Cancer Res. 2006, 12, 617-625).

CI value=$IC_{50}$ value of DFP-10917 in combined use (0.51 μM)/$IC_{50}$ value of DFP-10917 alone (1.53 μM)+$IC_{50}$ value of venetoclax in combined use (9.14 pM)/$IC_{50}$ value of venetoclax alone (96.8 pM)+[$IC_{50}$ value of DFP-10917 alone (1.53 μM)×$IC_{50}$ value of venetoclax alone (96.8 pM)]/[$IC_{50}$ value of DFP-10917 in combined use (0.51 μM)+$IC_{50}$ value of venetoclax in combined use (9.14 pM)]

The CI value has 1 as a standard. In the case of CI value=1, the CI value shows an additive effect. In the case of CI value<1, the CI value shows a synergistic effect.

Since the CI value was around 0.43 according to the above-mentioned expression, it was confirmed that the effect obtained by the combined use of DFP-10917 and venetoclax was a synergistic effect.

Example 3

Effect of Combined Use of DFP-10917 and Venetoclax in Animal Models

OCI-AML-2, which is an AML cell line, was hypodermically transplanted into NOD SCID mice ($5×10^6$ cells/mouse), and cancer-bearing model mice were produced.

An Alzet (R) osmotic mini-pump was implanted in the mouse body, and DFP-10917 was continuously administered in a dose of 3 mg/kg/day for 7 days.

Venetoclax was orally administered in a dose of 100 mg/kg/day for 14 days.

Only a vehicle was administered to control mice.

Administration was started seven days after transplant.

Figure 2:
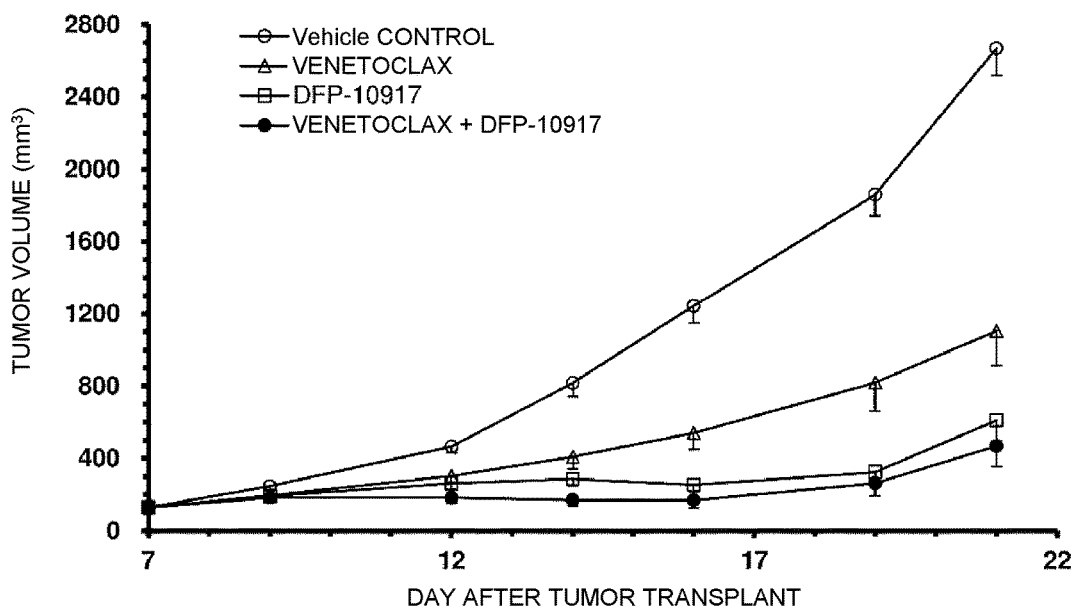
FIG. 2 is a graph showing the results obtained by investigating the cytostatic effects (tumor volume ($mm^3$)) of the combined use of DFP-10917 and venetoclax in animal models into which AML cells are transplanted.

FIG. 2 shows the results.

Figure 3:
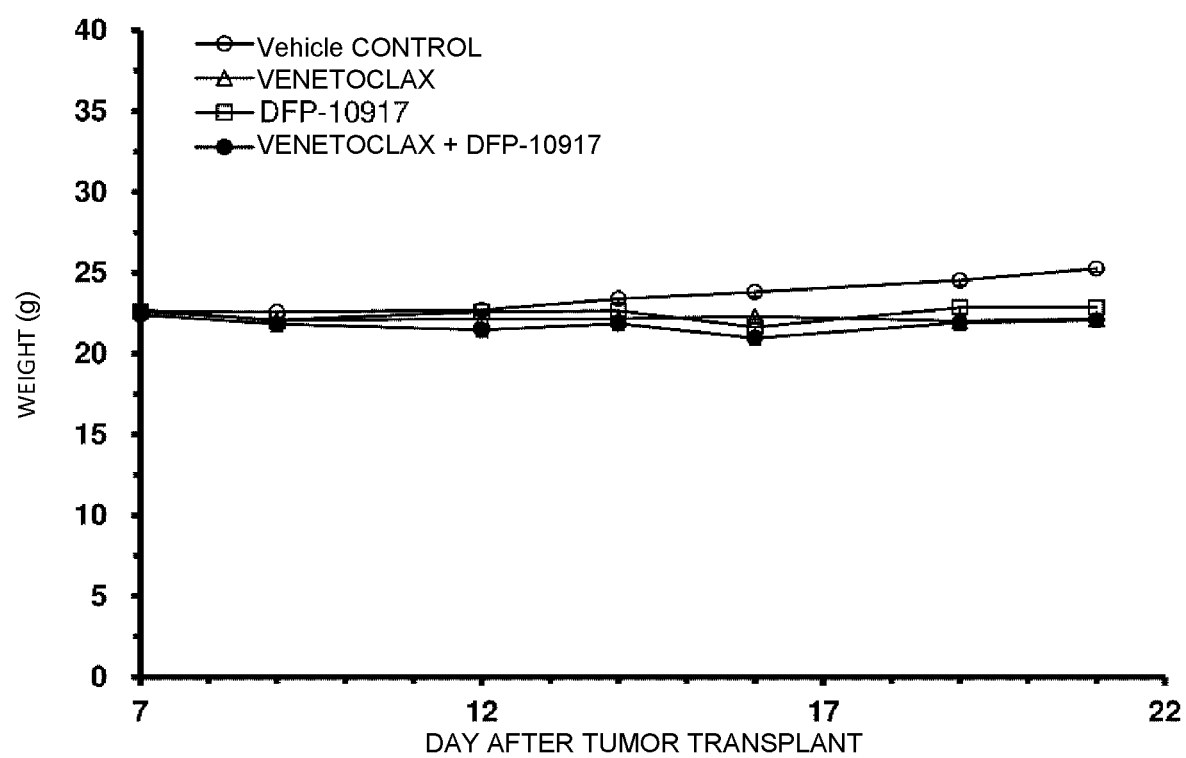
FIG. 3 is a graph showing the results obtained by measuring weights(g) after the administration of DFP-10917 and/or venetoclax over time in animal models into which AML cells are transplanted.

It was confirmed that when DFP-10917 and venetoclax was administered in combination, proliferation of the tumor was more suppressed as compared with the use of either alone. Meanwhile, a significant weight change was not observed in mice over the study period, and side effects (toxicity) of combined use of DFP-10917 and venetoclax were not observed (FIG. 3).

The invention claimed is:

1. A combined medicine, comprising 4-amino-1-(2-cyano-2-deoxy-(3-D-arabinofuranosyl)-2(1H)-pyrimidinone or a salt thereof in a dosage form for continuous intravenous infusion in an amount sufficient to provide an amount from 1 to 10 mg per 1 $m^2$ of body surface area of a patient per day over 168 to 336 hours, said patient having a blood cancer, and venetoclax or a salt thereof in a dosage form for oral administration to the patient.

2. The medicine according to claim 1, wherein blood cancer is selected from the group consisting of acute myelogenous leukemia (AML), chronic myelogenous leukemia (CIVIL), acute lymphocytic leukemia (ALL), chronic lymphocytic leukemia (CLL), a myeloproliferative neoplasm (MPN), and lymphoma.

3. The medicine according to claim 1, wherein venetoclax or the salt thereof is in a dosage form for oral administration in an amount sufficient to provide an amount from 20 to 400 mg/day to the patient.

4. The medicine according to claim 1, wherein the patient is a newly diagnosed and/or elderly patient.

5. A method for treating or ameliorating blood cancer, comprising administering to a patient with blood cancer 4-amino-1-(2-cyano-2-deoxy-(3-D-arabinofuranosyl)-2(1H)-pyrimidinone or a salt thereof by way of continuous intravenous infusion, in an amount from 1 to 10 mg per 1 $m^2$ of body surface area of the patient per day over 168 to 336 hours and venetoclax or a salt thereof orally.

6. The method according to claim 5, wherein the blood cancer is selected from the group consisting of acute myelogenous leukemia (AML), chronic myelogenous leukemia (CML), acute lymphocytic leukemia (ALL), chronic lymphocytic leukemia (CLL), a myeloproliferative neoplasm (MPN), and lymphoma.

7. The method according to claim 5, wherein venetoclax or a salt thereof is orally administered in an amount from 20 to 400 mg/day.

8. The method according to claim 5, wherein the patient is a newly diagnosed and/or elderly patient.

* * * * *

UNITED STATES PATENT AND TRADEMARK OFFICE
CERTIFICATE OF CORRECTION

PATENT NO.       : 11,957,701 B2
APPLICATION NO.  : 17/424805
DATED            : April 16, 2024
INVENTOR(S)      : Ishida et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 201 days.

Signed and Sealed this
Eighth Day of October, 2024

Katherine Kelly Vidal
*Director of the United States Patent and Trademark Office*